(12) United States Patent
Vickers (10) Patent No.: US 10,034,968 B2
(45) Date of Patent: Jul. 31, 2018

(54) MULTI-LAYERED ANTI-ADHESION DEVICE

(71) Applicant: Warsaw Orthopedic, Inc., Warsaw, IN (US)

(72) Inventor: Scott M. Vickers, Hernando, MS (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 15/427,809

(22) Filed: Feb. 8, 2017

(65) Prior Publication Data

US 2017/0143874 A1 May 25, 2017

Related U.S. Application Data

(62) Division of application No. 14/075,254, filed on Nov. 8, 2013, now Pat. No. 9,566,296.

(51) Int. Cl.
| | |
|---|---|
| *A61K 9/00* | (2006.01) |
| *A61L 31/04* | (2006.01) |
| *A61L 31/14* | (2006.01) |
| *A61F 2/00* | (2006.01) |

(52) U.S. Cl.
CPC .......... *A61L 31/041* (2013.01); *A61F 2/0063* (2013.01); *A61L 31/146* (2013.01); *A61L 31/148* (2013.01); *A61F 2002/0091* (2015.04); *A61F 2210/0076* (2013.01); *A61F 2230/0019* (2013.01); *A61F 2230/0069* (2013.01); *A61F 2250/0023* (2013.01); *A61F 2250/0067* (2013.01); *A61L 2300/232* (2013.01); *A61L 2300/424* (2013.01)

(58) Field of Classification Search
CPC .................................................... A61L 31/041
See application file for complete search history.

(56) References Cited

U.S. PATENT DOCUMENTS

| | | | |
|---|---|---|---|
| 5,866,165 A | 2/1999 | Liu et al. | |
| 6,896,904 B2 | 5/2005 | Spiro et al. | |
| 2002/0151650 A1 | 10/2002 | Pathak et al. | |
| 2004/0193088 A1 | 9/2004 | Looney et al. | |
| 2007/0031498 A1 | 2/2007 | Zong et al. | |
| 2007/0161109 A1* | 7/2007 | Archibald | A61F 2/0077 435/404 |
| 2011/0002999 A1 | 1/2011 | Chen et al. | |
| 2011/0274742 A1 | 11/2011 | Arinzeh et al. | |
| 2011/0276147 A1 | 11/2011 | Cook | A61L 27/46 623/23.51 |

FOREIGN PATENT DOCUMENTS

| | | | |
|---|---|---|---|
| WO | 2004105737 A2 | 12/2004 | |
| WO | WO 2013092339 A1 * | 6/2013 | ........... A61L 27/303 |
| WO | WO2013092339 A1 | 6/2013 | ............ A61L 27/30 |

* cited by examiner

*Primary Examiner* — Paul W Dickinson (57) ABSTRACT

Compositions and methods are provided for preparing an adhesion barrier in the form of a foldable or flexible biodegradable polymer matrix that effectively reduces, prevents or treats adhesions in a patient in need thereof. In one embodiment, the matrix comprises a first porous layer comprising collagen and a second porous layer comprising collagen and dextran, wherein the dextran is loaded in the second layer in an amount of from about 5% to about 90% by weight based on a total weight of the matrix. In some embodiments, the matrix prevents or reduces cell growth into the matrix so as to reduce or prevent adhesions. In some embodiments, the matrix is in a sheet or strip form that can be folded into a tube form.

7 Claims, 5 Drawing Sheets

| Formulation # | Animal # | Treated | | Control | |
|---|---|---|---|---|---|
| | | Tenacity | Extent | Tenacity | Extent |
| 1 | 1 | 0 | 0 | 3 | 2 |
| | 2 | 0 | 0 | 0 | 0 |
| | 3 | 1 | 1 | 1 | 1 |
| 2 | 1 | 1 | 1 | 0 | 0 |
| 3 | 1 | 0 | 0 | 1 | 1 |
| | 2 | 1 | 1 | 0 | 0 |
| | 3 | 1 | 1 | 3 | 3 |

FIG. 8

| Formulation # | Animal # | Treated | | Control | |
|---|---|---|---|---|---|
| | | Tenacity | Extent | Tenacity | Extent |
| 1-1 | 1 | 0 | 0 | 3 | 3 |
| | 2 | 1 | 1 | 3 | 3 |
| | 3 | 1 | 1 | 3 | 3 |
| 1-2 | 1 | 0 | 0 | 3 | 3 |
| | 2 | 1 | 1 | 3 | 3 |
| | 3 | 1 | 1 | 3 | 3 |
| | 4 | 1 | 1 | 3 | 3 |
| | 5 | 1 | 1 | 4 | 3 |
| | 6 | 1 | 1 | 4 | 3 |
| 1-3 | 1 | 0 | 0 | 2 | 3 |
| | 2 | 0 | 0 | 3 | 3 |
| | 3 | 1 | 1 | 2 | 2 |

MULTI-LAYERED ANTI-ADHESION DEVICE

This application is a divisional application of U.S. patent application Ser. No. 14/075,254 filed Nov. 8, 2013, entitled "MULTI-LAYERED ANTI-ADHESION DEVICE." This entire disclosure is incorporated herein by reference into the present disclosure.

BACKGROUND

Surgical adhesions are abnormal fibrous bands of scar tissue that can form inside the body as a result of the healing process that often follows open or minimally invasive surgical procedures including abdominal, gynecologic, cardiothoracic, spinal, plastic, vascular, ENT, ophthalmologic, urologic, neuro, or orthopedic surgery.

Surgical adhesions are typically connective tissue structures that form between adjacent injured areas within the body. Briefly, localized areas of injury trigger an inflammatory and healing response (clotting) that culminates in healing and scar tissue formation. If scarring results in the formation of fibrous tissue bands or adherence of adjacent anatomical structures (that should normally be separate), adhesion formation is said to have occurred.

Adhesions can range from flimsy, easily separable structures to dense, tenacious fibrous structures that can only be separated by surgical dissection. While many adhesions are benign, many adhesions can cause major pain. For example, adhesions to nerve structures (e.g., nerve root, spinal cord) and other vital structures after spinal surgery result in post-operative pain and make revision surgery difficult and potentially dangerous if necessary. More specifically, after spinal surgery if adhesions form they may cause tethering of spinal nerve roots and dorsal root ganglia, which often causes recurrent radicular pain that can be very debilitating to the patient and often leads to repeated surgical intervention.

Since most surgery involves a certain degree of trauma to the operative tissues, virtually any procedure (no matter how well executed) has the potential to result in the formation of clinically significant adhesion formation. Adhesions can be triggered by surgical trauma such as cutting, manipulation, retraction or suturing, as well as from inflammation, infection (e.g., fungal or mycobacterium), bleeding or the presence of a foreign body. Surgical trauma may also result from tissue drying, ischemia, or thermal injury. Due to the diverse etiology of surgical adhesions, the potential for formation exists regardless of whether the surgery is done in a so-called minimally invasive fashion (e.g., catheter-based therapies, laparoscopy) or in a standard open technique involving one or more relatively large incisions. Although a potential complication of any surgical intervention, surgical adhesions are particularly problematic in GI surgery (causing bowel obstruction), gynecological surgery (causing pain and/or infertility), tendon repairs (causing shortening and flexion deformities), joint capsule procedures (causing capsular contractures), and nerve and muscle repair procedures (causing diminished or lost function).

Surgical adhesions may cause various, often serious and unpredictable clinical complications; some of which manifest themselves only years after the original procedure was completed. Complications from surgical adhesions are a major cause of failed surgical therapy and are the leading cause of bowel obstruction and infertility. Other adhesion-related complications include chronic back or pelvic pain, intestinal obstruction, urethral obstruction and voiding dysfunction.

Relieving the post-surgical complications caused by adhesions generally requires another surgery. However, the subsequent surgery is further complicated by adhesions formed as a result of the previous surgery. In addition, the second surgery is likely to result in further adhesions and a continuing cycle of additional surgical complications.

Thus, there is a need to reduce, prevent, or treat adhesions. New compositions and methods are needed for manufacturing an adhesion barrier that reliably prevent in-growth of scar tissue and formation or reformation of adhesions at or near the target tissue site while an injured tissue heals.

SUMMARY

New compositions and methods are provided for preparing an adhesion barrier that effectively reduces, prevents or treats adhesions in a patient in need thereof. In various embodiments, an adhesion barrier is provided in the form of a matrix. The adhesion barrier retains dextran in portions of the barrier and thus prevents or reduces cell infiltration into the portions containing dextran. Additionally, in some embodiments, the barrier can have small pores or little pores in portions of the barrier to prevent cell growth into the matrix.

In various embodiments, an adhesion barrier is provided in the form of a matrix. The matrix is a foldable or flexible biodegradable polymer comprising a first porous layer comprising collagen and a second porous layer comprising collagen and dextran. The first layer is more porous than the second layer and the dextran is loaded in the second layer in an amount of from about 5% to about 90% by weight based on a total weight of the matrix. The matrix is configured to release from about 20% to about 90% of the dextran loaded in the matrix within 24 to 48 hours. In some embodiments, the matrix is in sheets or strips for application as an onlay to the wound site. In some embodiments, the matrix can be a cylindrical tube that can be applied to a tendon or nerve.

In some embodiments, an adhesion barrier is provided in the form of a matrix. The matrix is a foldable or flexible biodegradable polymer comprising a first layer comprising collagen, a second layer comprising dense collagen and a third layer comprising collagen and dextran. The dextran is loaded in the third layer in an amount of from about 5% to about 90% by weight based on a total weight of the matrix. The matrix is configured to release from about 20% to about 90% of the dextran loaded in the matrix within 24 to 48 hours.

In various embodiments, a method of treating adhesions in a patient is provided. The method comprises administering to the patient an adhesion barrier in the form of a foldable or flexible biodegradable polymer matrix comprising a first layer comprising collagen and a second layer comprising collagen and dextran, wherein the dextran is loaded in the second layer in an amount of from about 5% to about 90% by weight based on a total weight of the matrix, wherein the matrix is configured to release from about 20% to about 90% of the dextran loaded in the matrix within 24 to 48 hours.

In some embodiments, an adhesion barrier is provided in the form of a matrix. The matrix is foldable or flexible comprising a biodegradable polymer for reducing, preventing or treating adhesions in a patient in need thereof. The matrix comprises a first porous layer comprising collagen and a second porous layer comprising collagen and dextran. The second layer is more porous than the first layer to prevent diffusion of the dextran into the first layer. The dextran is loaded in the second layer in an amount of from about 5% to about 90% by weight based on a total weight of the matrix.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a matrix" includes one, two, three or more drug matrices. An "adhesion barrier" or "matrix," is the medium in which a cell inhibitor composition (e.g., dextran) is administered to the body. Thus, an adhesion barrier or matrix may comprise a physical structure to facilitate implantation and retention in a desired site (e.g., a disc space, a spinal canal, a tissue of the patient, particularly at or near a site of chronic pain, etc.). The adhesion barrier or matrix may also comprise the drug itself. Suitable materials for the adhesion barrier or matrix are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the matrix provides an optimal drug concentration gradient of the therapeutic agent at a distance of up to about 0.01 cm to about 20 cm from the administration site and comprises dextran. Alternatively or in addition to a matrix, a pump, an implant body or pellet may be utilized for drug delivery. In some embodiments, the matrix comprises a cell inhibitor composition, which comprises dextran.

A "therapeutically effective amount" or "effective amount" is such that when administered, the drug results in alteration of the biological activity, such as, for example, inhibition of inflammation, reduction or alleviation of pain or adhesions, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

The term "biodegradable" includes all or parts of the matrix that will degrade over time by the action of enzymes, by hydrolytic action and/or by other similar mechanisms in the human body. In various embodiments, "biodegradable" includes that the matrix can break down or degrade within the body to non-toxic components after or while a therapeutic agent has been or is being released. By "bioerodible" it is meant that the matrix will erode or degrade over time due, at least in part, to contact with substances found in the surrounding tissue, fluids or by cellular action. By "bioabsorbable" it is meant that the matrix will be broken down and absorbed within the human body, for example, by a cell or tissue. "Biocompatible" means that the matrix will not cause substantial tissue irritation or necrosis at the target tissue site.

In some embodiments, the second layer is more porous than the first layer to prevent diffusion of the dextran into the first layer but allows diffusion elsewhere. The cells will attach to a surface of the first layer, while preventing the dextran from diffusing into the first layer so that the dextran will not reach the attached cells. In various embodiments, the layers of the matrix act to store collagen and/or dextran. In some embodiments, the matrix stores dextran in a collagen layer. Various types of collagen may be used in the second layer such as, for example, the collagen materials described above with regard to the first layer.

In various embodiments, an adhesion barrier is provided in the form of a matrix. The adhesion barrier retains dextran in portions of the barrier and thus prevents or reduces cell infiltration into the portions containing dextran. Additionally, in some embodiments, the barrier can have small pores or little pores in portions of the barrier to prevent cell growth into the matrix.

In some embodiments, the matrix has multiple layers comprising pores that allow release and/or retention of the drug from the matrix. The matrix will allow fluid in the matrix to displace the drug. However, cell infiltration into the matrix will be prevented by the size of the pores of the matrix, the composition of the layers and the drug that is selected. In this way, in some embodiments, the matrix should not function as a tissue scaffold and allow tissue growth. Rather, the matrix will solely be utilized for drug delivery. In some embodiments, the pores of a layer in the matrix will be about 0.05 to 200 microns. This pore size will prevent cells from infiltrating the matrix and laying down scaffolding cells. In some embodiments, where there are little or no pores, the drug will elute out from the matrix by the action of enzymes, by hydrolytic action and/or by other similar mechanisms in the human body. In some embodiments, pores of a layer of the matrix has pores that are greater than 250 to 1000 microns to allow certain types of cell to infiltrate the biodegradable porous matrix and lay down scaffolding cells. In some embodiments, the matrix is part tissue scaffold and part tissue growth device. The pore sizes will range from about 0.05 to 200 microns for preventing cell infiltration and from about than 250 to 1000 microns or greater to allow cell infiltration into the device.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the matrix, or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustained release and immediate release) may be used in conjunction. The sustained release and immediate release may be in one or more of the same matrices. In various embodiments, the sustained release and immediate release may be part of separate matrices. For example a bolus or immediate release formulation of a dextran sulfate composition may be placed at or near the target site and a sustain release formulation may also be placed at or near the same site. Thus, even after the bolus becomes completely accessible, the sustained release formulation would continue to provide the active ingredient for the intended tissue.

In various embodiments, the matrix can be designed to cause an initial burst dose of therapeutic agent within the first twenty-four to forty-eight or seventy-two hours after implantation. "Initial burst" or "burst effect" or "bolus dose" refers to the release of therapeutic agent from the matrix during the first twenty-four hours to forty-eight or seventy-two hours after the matrix comes in contact with an aqueous fluid (e.g., synovial fluid, cerebral spinal fluid, etc.). The "burst effect" is believed to be due to the increased release of therapeutic agent from the matrix. In alternative embodiments, the matrix (e.g., gel) is designed to avoid or reduce this initial burst effect (e.g., by applying an outer polymer coating to a layer of the matrix). In some embodiments, the matrix has a burst release surface or layer that releases about 5%, 10%, 15%, 20%, 25%, 30%, 35%, 45%, 50%, 55%, 60%, 65%, 70%, 75%, 80%, 85%, 90% to about 95% of the cell migration inhibitor (e.g., dextran) over 24 or 48 hours.

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient. "Reducing adhesion formation" includes a decrease in adhesion formation and does not require complete alleviation of adhesion signs or symptoms, and does not require a cure. In various embodiments, reducing adhesion formation includes even a marginal decrease in adhesion formation by for example 5%, 10%, 15%, 20%, 25%, 30%, 35%, 40%, 45% or higher decreases in adhesion formation or compared to matrices without dextran. By way of example, the administration of the effective dosage of a dextran sulfate composition may be used to prevent, treat or relieve adhesion formation for different conditions. These conditions may comprise postoperative surgical sites.

"Treating adhesions," refers to administering a composition that reverses, alleviates, reduces, and/or inhibits the progression and/or severity of adhesions, or reduces the likelihood of recurrence and/or the severity of recurrent adhesions. "Treating adhesions" also refers to administering or applying a composition that reverses, alleviates, reduces, inhibits the progression of, or reduces the likelihood of recurrence and/or severity of one or more symptoms of adhesions (e.g., pain, bowel obstruction, infertility, etc.). In various embodiments, treating adhesions may be part of a protocol and also include performing a procedure (e.g., surgery to reduce adhesions). Thus "treating adhesions" involves administering or applying a therapeutic composition and/or procedure once adhesion(s) have already formed following an insult or stimulus.

The term "implantable" as utilized herein refers to a biocompatible device (e.g., matrix) retaining potential for successful placement within a mammal. The expression "implantable device" and expressions of the like import as utilized herein refers to an object implantable through surgery, injection, or other suitable means whose primary function is achieved either through its physical presence or mechanical properties.

"Cell inhibitor compositions" that the matrix may contain include, but are not limited to anionic polymers such as, for example, dextran, dextran sulfate (DX) and pentosan polysulfate (PS). Additionally, natural proteoglycans, or the glycosaminoglycan moieties of proteoglycans, including dermatan sulfate (DS), chondroitin sulfate (CS), keratan sulfate (KS), heparan sulfate (HS), and heparin (FIN) may be used. Alginate (AL) also may be used. At a suitable concentration, the foregoing molecules can inhibit fibroblast and/or myofibroblast invasion or migration, even in the presence of suitable migration promoting substrates, such as laminin. Molecules and compositions comprising DX, to inhibit, prevent or regulate fibroblast invasion and fibrosis can be used. For example, molecules comprising KS, CS, DS, HS, or FIN include but are not limited to the disaccharide, glycosaminoglycan, and proteoglycan structures.

Dextran

According to some embodiments, a composition and method are provided for preparing a foldable or flexible biodegradable matrix for reducing and/or eliminating adhesion formation after surgery is performed. In some embodiments, the method involves the incorporating a cell migration inhibiting compound, such as dextran (e.g., dextran sulfate), into a porous biodegradable matrix such as a sponge or sheet. Use of this device (e.g., sponge, sheet) includes placing the device at the tissue site to be protected from scar formation, such as over a nerve structure or other vital structures, after the necessary surgery has been performed.

The foldable or flexible biodegradable matrix disclosed herein may be formed by mixing solutions of dextran or dextran sulfate and a matrix forming material such as a protein, polysaccharide or mixture thereof to form a slurry. Subsequently, the slurry can be formed into a foldable or flexible biodegradable matrix of any shape by lyophilization, or wet-laying and air drying in molds of the desired shape. Thereafter, the foldable or flexible biodegradable matrix comprising dextran or dextran sulfate can comprise layers that include collagen, dextran or dextran sulfate and/or a combination thereof, which when applied to a surgical site can prevent or reduce the growth of adhesion forming cells from the surgical site. In some embodiments, the matrix comprises multiple layers that comprise varying porosities.

In some embodiments, the foldable or flexible biodegradable matrix comprises dextran or dextran sulfate in an amount of from about 5 wt. % to about 70 wt. % based on the weight of the matrix. In other embodiments, the matrix comprises dextran or dextran sulfate in an amount of from about 10 wt. % to about 50 wt. % based on the weight of the matrix. In some embodiments, the foldable or flexible biodegradable matrix comprises dextran or dextran sulfate in an amount of from about 70 wt. % to about 99 wt. % based on the weight of the matrix. In some embodiments, the loading of the cell migration inhibition agent (e.g., dextran) is from about 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, to about 99 wt. % based on the weight of the matrix.

In some embodiments, there is a higher loading of dextran or dextran sulfate, e.g., at least 20 wt. %, at least 25 wt. %, at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, at least 75 wt. %, at least 80 wt. %, at least 85 wt. %, or at least 90 wt. %. In some embodiments, the foldable or flexible biodegradable matrix has multiple layers which can be used to reduce or prevent adhesion formation by, among other things, inhibiting cell migration.

Dextran is a complex, branched glucan (polysaccharide made of many glucose molecules) composed of chains of varying lengths (from 3 to 2000 kilodaltons). It is used medicinally as an antithrombotic (anti-platelet), to reduce blood viscosity, and as a volume expander in anemia. The antithrombotic effect of dextran is mediated through its binding of erythrocytes, platelets, and vascular endothelium, increasing their electronegativity and thus reducing erythrocyte aggregation and platelet adhesiveness.

Dextran used in the composition and/or method of preparing the foldable or flexible biodegradable matrix of the current disclosure can have a wide range of average molecular weights higher than about 500,000 Daltons. In various embodiments, the dextran can have a molecular weight of about 600,000, 625,000, 650,000, 675,000, 700,000, 725,000, 750,000, 775,000, 800,000, 825,000, 850,000, 875,000, 900,000, 925,000, 950,000 and/or 975,000 Daltons. In some embodiments, the dextran can have an average molecular weight of about 1.5 million to about 2.5 million Daltons. In various embodiments, the dextran can have an average molecular weight lower than 500,000 Daltons. In some embodiments, the dextran can have a molecular weight of about 3,000, 30,000, 60,000, 90,000, 120,000, 150,000, 180,000, 210,000, 240,000, 270,000, 300,000, 330,000, 360,000, 390,000, 420,000, 450,000 and/or 480,000 Daltons. In some embodiments, the dextran can have a molecular weight of 40,000 to 500,000 Daltons. In various embodiments, the dextran can have a molecular weight of 40,000, 50,000, 60,000, 70,000, 80,000, 90,000, 100,000, 200,000, 300,000, 400,000 and/or 500,000 Daltons.

In various embodiments, the dextran comprises dextran sulfate. In some embodiments, the sulfur content of the dextran can be increased, e.g., the number of sulfate groups per glucosyl residue in the dextran chain. The average sulfur content for dextran sulfate may be about 10 to 25%, such as 15% to 20% or 16% to 19%, corresponding to about two sulfate groups per glucosyl residue. Dextran sulfates are supplied as sodium salts, which are soluble and stable in water. In various embodiments, dextran sulfate contains approximately 17% sulfur which is equivalent to approximately 2.3 sulfate groups per glycol residue.

The amounts of dextran or dextran sulfate in the foldable or flexible biodegradable matrix will depend on the severity of the condition, and on the patient to be treated, as well as the matrix used and administration route employed. The concentration of the dextran used should not be too high in order to minimize any side-effects associated with dextran. In clinical situations, suitable doses of dextran in humans are those that give a mean blood concentration below 5 mg/ml. In various embodiments, a concentration range for dextran or dextran sulfate is between 2.0 mg/ml and 10 mg/ml. In some embodiments, the concentration of dextran or dextran sulfate is about 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0 9.25, 9.5, 9.75 and/or 10.0 mg/ml. The above-identified dosages are examples of preferred dosages of the average case. However, there can be individual instances where higher or lower dosage ranges are merited, and such are within the scope of the invention.

In some embodiments, the foldable or flexible biodegradable matrix can comprise dextran or dextran sulfate uniformly disposed throughout it. In some embodiments, the dextran or dextran sulfate can be disposed at discrete regions of the biodegradable porous matrix. In some embodiments, the dextran or dextran sulfate can be disposed at discrete layers within the matrix. In some embodiments, the matrix can comprise fibers and/or particles having the dextran or dextran sulfate disposed within the fibers and/or particles (e.g., electrospun dextran fibers). The fibers may, in some embodiments, have a diameter ranging from 0.55 microns to 1.75 microns. The particles may, in some embodiments, have a diameter ranging from 0.25 microns to 1.5 microns.

The amount of dextran or dextran sulfate per matrix can vary widely, depending on the size of device that is being manufactured, with typical device formulations using from about 0.001-0.2 g of dextran per device. However, the range can be extended widely, e.g. from as low as about 0.0001 g or less (for small devices) to as high as 1.0 g per device, for large devices. In some embodiments, it may be helpful to use lesser amounts of dextran (e.g. about 0.00001 to about 0.0001 g of dextran per device) in order to concentrate the active agents that are delivered by the device into a smaller volume. In some embodiments, the foldable or flexible biodegradable matrix comprises from about 5 wt. % to about 70 wt. % dextran based on the total weight % of the matrix.

For example, the dextran can comprise 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70 wt. % of the total weight percent of the matrix. In various embodiments, the matrix preferably comprises about 10 wt. % to about 50 wt. % of dextran based on the total weight % of the matrix.

In some embodiments, the dextran can be in polymer form that has acetate, propionate, and/or succinate groups attached via ester linkages to a significant fraction of the dextran polymer's hydroxyl groups. In one embodiment, the dextran polymer comprises dextran acetate, dextran propionate, dextran succinate, dextran acetate propionate, dextran acetate succinate, dextran propionate succinate, dextran acetate propionate succinate, dextran sulfate, or mixtures thereof. In another embodiment, the dextran polymer comprises dextran acetate succinate, dextran propionate succinate, dextran acetate propionate succinate, dextran sulfate or mixtures thereof. In another embodiment, the dextran polymer comprises dextran acetate succinate. In yet another embodiment, the dextran polymer comprises dextran propionate succinate.

In some embodiments, the dextran can be an aminated dextran that can have an average molecular weight greater than about 500,000 Daltons, and an amine substitution level of about 1% to about 65%, more particularly about 1% to about 40%, more particularly about 1% to about 5%, and more particularly about 2% to about 3%.

Other compounds other than dextran sulfate that have the property of inhibiting cell migration may be used in addition to, or instead of, dextran sulfate.

Matrix Materials

In various embodiments, a foldable or flexible biodegradable matrix comprising multiple layers is provided. In some embodiments, the matrix is formed layer by layer. For example, liquids of matrix forming materials specific to each separate layer of the matrix is admixed with additional materials (e.g., a liquid of dextran or dextran sulfate, pore forming agents, etc.) to form multiple slurries. Each slurry is lyophilized in molds of the desired shape (e.g., a sheet) and then the molded shapes are joined. The result is a foldable or flexible biodegradable matrix comprising layers and bearing dextran or any other material that can inhibit adhesion forming cells. In some embodiments, the solution of dextran or dextran sulfate comprises 0.05M acetic acid and the solution of matrix forming material can also comprises 0.05M acetic acid. In various embodiments, the matrix forming material can be a protein, a polymer, a polysaccharide or a combination thereof. In some embodiments, the matrix forming material can be a protein which comprises collagen, albumin, fibrinogen, fibronectin, vitronectin, laminin or a mixture thereof. In other embodiments, the matrix forming material can be a polysaccharide which comprises hyaluronic acid, dextran, dextran sulfate, chondroitin sulfate, dermatan sulfate, keratan sulfate, heparin, heparin sulfate, chitosan, chitin, alginate or a mixture thereof. As used herein, the term "matrix forming material" includes the polysaccharides or proteins and their salts such as the sodium, potassium, magnesium, calcium, and the like, salts. Preferred forms of starting material of the matrix forming material include those which have been approved for human use.

In some embodiments, the matrix forming material comprises collagen. The starting material for producing collagen can be purified collage, native collagen or modified collage of any type. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises a collagen that is in the entire matrix or is in a layer of the matrix in an amount of from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

The type of polysaccharides which may be utilized include hyaluronic acid, chondroitin sulfate, dermatan sulfate, keratan sulfate, heparan, heparan sulfate, dextran, dextran sulfate, alginate, and other long chain polysaccharides. Typically, the polysaccharide can have an average molecular weight of about 1,000 to 10,000,000 DA. Hyaluronic acid is a natural component of the cartilage extracellular matrix, and it is readily sterilized, is biodegradable and can be produced in a wide range of consistencies and formats. It is generally biocompatible and its resorption characteristics can be controlled by the manipulation of monomers to polymer forms, most commonly through the esterification of the carboxylic groups of the glucuronic acid residues.

In some embodiments, the matrix may comprise one or more bioerodible polymers, bioabsorbable polymers, biodegradable biopolymers, synthetic polymers, copolymers and copolymer blends or combinations thereof. Exemplary materials may include biopolymers and synthetic polymers such as human skin, human hair, bone sheets, collagen, fat, thin cross-linked sheets containing fibers and/or fibers and chips, degradable sheets made from polyethylene glycol (PEG), chitosan sheets, alginate sheets, cellulose sheets, hyaluronic acid sheet, as well as copolymer blends of poly (lactide-co-glycolide) PLGA.

In some embodiments, the biodegradable porous matrix may comprise natural and/or synthetic material. For example, the tissue scaffold and/or a layer or layers of the matrix may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, PEAs, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D, L-lactide, or L-lactide, ,-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In various embodiments, the matrix comprises a pore forming agent and/or a plasticizer. Plasticizers and/or pore forming agents impart malleability to the resulting matrix. Additionally, plasticizers and/or pore forming agents make various layers of the matrix porous and/or more porous after implantation. In some embodiments, the plasticizers and/or pore forming agents include but are not limited to MgO (e.g., 1 wt. %), mPEG, propylene glycol, mannitol, trehalose, TBO-Ac, Span-65, Span-85, pluronic F127, sorbitol, xylitol, isomalt, erithritol, cyclodextrin, maltodextrin, pluronic F68, CaCl, dextran, dextran sulphate, dextran phosphate, hydroxypropylcellulose, ethylcellulose, PEG 1500, PEG 400, PEG3350, acetyl tributyl citrate, butyl benzyl phthalate, butyl phthalyl butyl glycolate, dibutyl phthalate, dibutyl sebacate, diethyl phthalate, diethylene glycol dibenzoate, dipropylene glycol, dipropylene glycol dibenzoate, ethyl phthalyl ethyl glycolate, ethyl-p-toluene sulfonamide, hexylene glycol, methyl phthalyl ethyl glycolate, polyoxyethylene aryl ether and tributoxyethyl phthalate or combinations thereof. Other plasticizers that may be utilized include esters of ortho, iso and terephthalate, esters of citric acid, esters of 1,2-, 1,3- and 1,4-cyclohexane dicarboxylic acid, and anhydrides or combinations thereof. In some embodiments, the particle size of the plasticizer is about 1 to about 250 microns, about 1 to about 100 microns or about 1 to about 10 microns. In some embodiments, the plasticizer and or pore forming agent is amorphous and/or crystalline.

In some embodiments, the matrix can be crosslinked to improve strength and integrity of the matrix. Any suitable technique for crosslinking can be used. These include for example the use of chemical crosslinkers such as gluteraldehyde, formaldehyde, 1,4-butanediol diglycidyl ether, hydroxypyridinium, and hydroxylysylpyridinium. Other crosslinking techniques include irradiation (e.g., E-beam or gamma irradiation), light (e.g., ultraviolet light or other wavelengths of light using an appropriate initiator), or via photooxidation. The matrix can also be crosslinked under dehydrothermal conditions or acidic conditions. For example, the matrix can be crosslinked under dehydrothermal conditions by subjecting the composition to a vacuum at elevated temperature. These and other known crosslinking methods will be suitable.

Physical Forms of a Foldable or Flexible Biodegradable Matrix

A foldable or flexible biodegradable matrix of the present disclosure may be formulated in several physical forms, including multi-layered sponge-like forms. The sponge configuration allows for the resulting adhesion prevention device to occupy a larger volumetric space (than a thin sheet) adjacent to the nerve structure being protected. Further, the sponge will also absorb body fluids at the surgical site and will better stay in place at the nerve or vital structure. Several alternate designs are possible including use of various biomaterial carriers (other than collagen) and forms and shapes. These include sheets, strips or onlays that can be folded into a cylindrical or tubular shape.

Generally, a foldable or flexible biodegradable matrix according to the present disclosure may comprise a single or multi-layered structure capable of at least partially retaining a substance, such as a cell inhibitor composition (e.g., dextran) provided therein, until the structure is placed at a surgical site. In some examples, upon placement, the matrix may facilitate transfer of the substance and/or materials surrounding the surgical site. The matrix may participate in, control, or otherwise adjust, the release and/or retention of the substance and/or penetration of the biodegradable porous matrix by surrounding materials, such as cells or tissues. Alternately, the matrix may include at least an impenetrable portion or a layer for preventing release of the substance and/or penetration of a portion of the matrix by surrounding materials.

Figure 1:
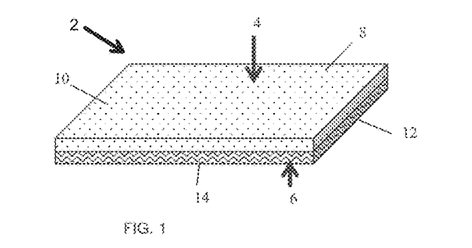
FIG. 1 depicts a front view of an exemplary device comprising a foldable or flexible biodegradable anti-adhesion matrix according to an aspect of the present application. In some embodiments, the matrix comprises a first layer and a second layer. In some embodiments, the matrix comprises a plurality of layers comprising 2, 3, 4, 5, 6 or more layers. In some embodiments, the first layer comprises collagen and the second layer comprises collagen and dextran. In some embodiments, the plurality of layers may comprise collagen, collagen and dextran and/or no dextran.

In various embodiments, the matrix is a foldable or flexible biodegradable matrix 2 (FIG. 1). The matrix is capable of folding on itself and can be shaped into various forms. In some embodiments, the matrix cannot be torn or broken when folded or rolled and can be easily handled using small surgical instruments. In some embodiments, the matrix is disposed with a portion of a spinal cord and will prevent adhesion formation. In various embodiments, the matrix is a multi-layered matrix comprising a first layer 4 and a second layer 6. The first layer is porous 8 and comprises collagen 10. In some embodiments, the first layer is highly porous and has a pore size from about 250 to about 500 microns, or about 250 to about 1000 microns or about 500 to about 2000 microns. In some embodiments, multiple pore sizes ranging from about 250 to about 1000 microns or about 500 microns to about 2000 microns or larger can be dispersed throughout the first layer. The large pore size allows cells to infiltrate and attach to the first layer to form scaffolding cells.

Various types of collagen may be used in the first layer. The collagen can be purified collage, native collagen or modified collage of any type. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen in the first layer in an amount from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

The second layer 6 comprises collagen 12 and dextran 14. In various embodiments, the second layer is less porous than the first layer. In various embodiments, the second layer has a pore size from about 0.05 to about 2 microns. In some embodiments, multiple pore sizes ranging from about 0.05 to about 200 microns or about 2 microns to 100 microns can be dispersed throughout the second layer. The small pore size in the second layer is configured to prevent diffusion of the dextran into the first layer. In some embodiments, the second layer has little or no pores and the drug will elute out from the matrix by the action of enzymes, by hydrolytic action and/or by other similar mechanisms in the human body. The drug is released from the second layer to keep adhesion forming cells away from the targeted surgical site.

In some embodiments, the second layer is more porous than the first layer to prevent diffusion of the dextran into the first layer but allows diffusion elsewhere. The cells will attach to a surface of the first layer, while preventing the dextran from diffusing into the first layer so that the dextran will not reach the attached cells. In various embodiments, the layers of the matrix act to store collagen and/or dextran. In some embodiments, the matrix stores dextran in a collagen layer. Various types of collagen may be used in the second layer such as, for example, the collagen materials described above with regard to the first layer.

In some embodiments, the matrix comprises collagen in the second layer in an amount from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

In various embodiments, the dextran is loaded in the second layer in an amount from about 5% to about 90% by weight based on a total weight of the matrix. In some embodiments, the dextran is dextran sulfate. In various embodiments, the dextran sulfate comprises from about 5.0 wt. % to about 70 wt. % of the entire matrix. In some embodiments, the dextran sulfate is loaded in the second layer in an amount from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

In various embodiments, the matrix is configured to release and/or retain about 20% to about 90% of the dextran loaded in the matrix within 24 to 48 hours.

In some embodiments, the matrix comprises a plurality of layers. In various embodiments, the matrix comprises 2, 3, 4, 5, 6 or more layers. In some embodiments, the plurality of layers comprises alternate layers of collagen and dextran, collagen and/or no dextran. In some embodiments, the plurality of layers comprises no dextran. In various embodiments, the plurality of layers differ and/or alternate in pore size. In some embodiments, the plurality of layers comprises layers that have a high porosity and layers that have a low porosity.

Figure 2:
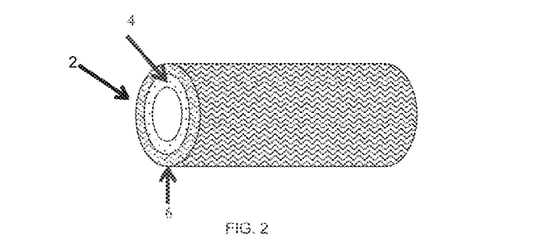
FIG. 2 provides a side perspective view of an exemplary device comprising a foldable or flexible biodegradable anti-adhesion matrix according to an aspect of the present application.

In some embodiments, the foldable or flexible biodegradable matrix 2 can be folded into a wrap configuration (FIG. 2). In the wrap configuration, the second layer is on the outside of the wrap and the first layer is on the inside of the wrap. In this embodiment, tissues will adhere to the inside of the wrap within the first layer. The second layer will prevent the cells from exiting the wrap and forming scaffolding cells.

Figure 3:
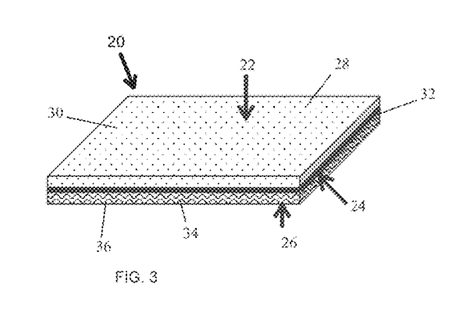
FIG. 3 depicts a front view of an exemplary device comprising a foldable or flexible biodegradable anti-adhesion matrix according to an aspect of the present application.

In various embodiments, a foldable or flexible biodegradable matrix 20 comprises a first layer 22, a second layer 24 and a third layer 26 (FIG. 3). In some embodiments, the matrix is disposed in a portion of a tendon or nerve that is in need of repair (e.g., tendon tear) and will prevent adhesion formation. The first layer is porous 28 and comprises collagen 30. In some embodiments, the first layer is highly porous and has a pore size from about 250 to about 2000 microns. In some embodiments, multiple pore sizes ranging from about 250 to about 2000 microns can be dispersed throughout the first layer. The large pore size allows cells to infiltrate and attach to the first layer to form scaffolding cells. Various types of collagen may be used in the first layer such as, for example, any of the collagen materials described herein.

In some embodiments, the matrix comprises collagen in the first layer in an amount from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

The second layer 24 comprises dense collagen 32. The second layer is non-porous or minimally porous. In some embodiments, the dense collagen is type II collagen. In various embodiments, the dense collagen can be any of the collagen materials described herein. In some embodiments, the second layer is thinner than the first layer and the third layer. In some embodiments, the second layer is the same thickness as the first layer and the third layer.

In some embodiments, the matrix comprises collagen in the third layer in an amount from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

The third layer comprises collagen 34 and dextran 36. The third layer is less porous than the first layer but is more porous than the second layer. In various embodiments, the third layer has a pore size from about 0.05 to about 200 microns or 10 to 100 microns. In some embodiments, multiple pore sizes ranging from about 0.05 to about 200 microns can be dispersed throughout the third layer. The small pore size of the third layer combined with the dense collagenous, non-porous or minimally porous second layer, are configured to prevent diffusion of the dextran into the first layer. In some embodiments, the third layer has little or no pores and the drug will elute out from the matrix by the action of enzymes, by hydrolytic action and/or by other similar mechanisms in the human body. The drug is released from the third layer to keep adhesion forming cells away from the targeted surgical site. Various types of collagen may be used in the third layer such as, for example, the collagen materials described herein.

In some embodiments, the matrix comprises collagen in the third layer in an amount from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

In various embodiments, the dextran is loaded in the third layer in an amount from about 5% to about 90% by weight based on a total weight of the matrix. In some embodiments, the dextran is dextran sulfate. In various embodiments, the dextran sulfate comprises from about 5.0 wt. % to about 70 wt. % of the entire matrix. In some embodiments, the dextran sulfate is loaded in the second layer in an amount from about 0.25%, 0.5%, 0.75%, 1 wt. %, 2 wt. %, 3 wt. %, 4 wt. %, 5 wt. %, 10%, 15%, 20%, 25%, 30%, 35%, 45%, 50%, 55%, 60%, 65%, 70%, 75%, 80%, 85%, 90%, to about 99 wt. %.

Figure 4:
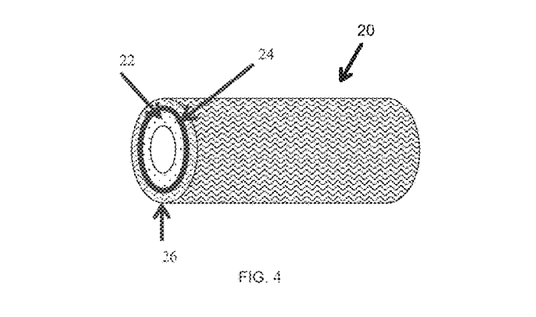
FIG. 4 provides a side perspective view of an exemplary device comprising a foldable or flexible biodegradable anti-adhesion matrix according to an aspect of the present application.

In some embodiments, the foldable or flexible biodegradable matrix 20 can be folded into a wrap configuration (FIG. 4). In the wrap configuration, the third layer is on the outside of the wrap and the first layer is on the inside of the wrap. The second layer is disposed between the first layer and the third layer. In this embodiment, tissues will adhere to the inside of the wrap within the first layer. The combination of the second layer and third layer will prevent the cells from exiting the wrap and forming scaffolding cells.

In various embodiments, the matrices described in this disclosure, are relatively soft sponge forms that can be adjusted for a surgical site by surgical scissors or scalpel. In certain embodiments, the length L of the overall matrix 2 and/or 20 (FIGS. 1-4) will range from about 1 cm to about 30 cm, the width W will range from about 1 cm to about 30 cm, and the thickness T will range from about 0.1 cm to about 4 cm. Length L may range from about 3 to about 6 cm, width W may range from about 3 to about 3 cm, and thickness T may range from about 0.5 to about 2 cm.

As to volume, advantageous matrices can have a total volume of at least about 1 cubic centimeters (cc), e.g. in the range of about 1 cc to about 50 cc, and more typically in the range of about 3 cc to about 6 cc, although both smaller and larger overall volumes may also be used. Similarly, the volume of the pieces into which the implant bodies are configured to be separated may range from about 1 cc to about 50 cc, more typically in the range of about 3 cc to about 6 cc, although other piece volumes will also be suitable in broader aspects of the present principles.

In some embodiments, the matrix has a thickness of from 0.20 mm to 6 mm, or from about 0.6 mm to about 3 mm, or 0.5 mm to about 2 mm. Clearly, different surgical sites (e.g., laminectomy, laminotomy, discectomy, facetectomy) may require different thicknesses for the matrix.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the matrix may be tailored to the site at which it is to be situated. For example, it may be in the shape of a tube, morsel, plug, pin, rod, sphere cube, peg, cylinder, block, wedge or sheet. In various embodiments, pre-defined shapes of the matrix include a shape that has a thicker middle section where the matrix is utilized to fill a larger void surgical space. In some embodiments, the matrix can have the shape of letter H in order to fit a spinal laminectomy surgical site.

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent (including one or more dextran compositions) may be disposed on or in the layers of the foldable or flexible biodegradable matrix by hand by soaking, electro spraying, ionization spraying or impregnating, vibratory dispersion (including sonication), nozzle spraying, compressed-air-assisted spraying, brushing and/or pouring.

Drugs, growth factors, polypeptides, proteins, cDNA, gene constructs and other therapeutic agents may also be included in the foldable or flexible biodegradable matrix and can be entrapped within the sponge either by mixing the agent with one of the two derivatives before gelatinization, or diffusion from a drug solution into the sponge after their formation. The therapeutic agent may also be covalently linked to the foldable or flexible biodegradable matrix.

As will be understood by those of skill in the art, the amount of agent to be immobilized or encapsulated within the carrier will vary depending upon the intended target, but will usually be in the range of pictogram, nanogram, milligram, to gram quantities.

A matrix prepared by methods of the present disclosure may be administered through implantation or direct application depending on the intended application. In some embodiments, the matrix may comprise sterile and/or preservative free material. The matrix can be implanted by hand or machine in procedures such as for example, laparoscopic, arthroscopic, neuroendoscopic, endoscopic, rectoscopic procedures or the like.

In some embodiments, the matrix may be in the form of a porous collagen sponge that can be spray coated, embedded or imparted with a cell inhibitor composition such as dextran sulfate, and as the sponge degrades, the composition may be gradually released over time.

In some embodiments, the initial burst surfaces can be disposed on the edges of a layer of the matrix so that upon contact with the target tissue site, the edges will begin to release the cell inhibitor composition (e.g., dextran). In some embodiments, the core of the matrix, a layer, or multiple layers can comprise dense, entangled polymers and have the cell inhibitor composition (e.g., dextran) to provide slower release of the cell inhibitor composition.

Alternatively, the cell inhibitor composition (e.g., dextran) can be disposed homogenously throughout a layer of the biodegradable porous matrix to provide continuous extended release of the cell inhibitor composition. In some embodiments, the cell inhibitor composition can be layered in the foldable or flexible biodegradable matrix with some portions having different concentrations to provide burst release and then slower release of the cell inhibitor composition.

In various embodiments, the ratio of free to bound dextran disposed within the foldable or flexible biodegradable matrix is about 90:10, 80:20, 70:30, 60:40, 50:50, 40:60, 30:70, 20:80 and 10:90. In some embodiments, the ratio of free to bound dextran is dependent on the manner in which dextran is distributed within the foldable or flexible biodegradable matrix, the degree of crosslinking performed, the amount of dextran added to the matrix and/or the amount of time that has elapsed. As bodily fluid contacts the matrix, dextran is released (also referred to as free dextran) and some remains in or on the matrix and is also referred to as bound dextran.

In some embodiments, the various different forms of the matrix are flexible and have a modulus of elasticity in the range of about $1\times10^2$ to about $6\times10^5$ dynes/cm$^2$, or $2\times10^4$ to about $5\times10^5$ dynes/cm$^2$, or $5\times10^4$ dynes/cm$^2$ to about $5\times10^5$ dynes/cm$^2$.

In some embodiments, the matrix may comprise a polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the matrix may have a burst release surface that releases about 10%, 15%, 20%, 25%, 30%, 35%, 45%, 50, 55%, 60%, 65%, 70%, 75%, 80%, 85%, 90%, 95%, 96%, 97%, 98%, to 99% of the cell inhibitor composition over 24 or 48 hours.

In some embodiments, the matrix may retain about 10%, 15%, 20%, 25%, 30%, 35%, 45%, 50, 55%, 60%, 65%, 70%, 75%, 80%, 85%, 90%, 95%, 96%, 97%, 98%, to 99% of the cell inhibitor composition over 24 or 48 hours.

Delivery of the Matrix

It will be appreciated by those with skill in the art that the matrix can be administered to the target site using a "cannula" or "needle" that can be a part of a drug delivery device e.g., a syringe, a gun drug delivery device, or any medical device suitable for the application of a drug to a targeted organ or anatomic region. The cannula or needle is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the matrix implanted at this site for treating the condition. Typically, the transforaminal approach involves approaching the intervertebral space through the intervertebral foramina.

Some examples of lengths of the cannula or needle may include, but are not limited to, from about 15 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 (mm). The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the matrix, the cannula or needle includes dose radiographic markers that indicate location at or near the site beneath the skin, so that the user may accurately position the matrix at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

In various embodiments, a method for delivering a therapeutic agent into a site of a patient is provided, the method comprising providing an implantable device comprising a porous matrix including a cell inhibitor composition (e.g., dextran), inserting a cannula at or near a target tissue site and implanting the matrix at the target site beneath the skin of the patient.

Advantageously, a matrix can be easily delivered to the target tissue site (e.g., abdomen, synovial joint, at or near the spinal column, etc.) and reduce, prevent or treat adhesion formation. In this way, accurate and precise implantation of the matrix in a minimally invasive procedure can be accomplished with minimal physical and psychological trauma to a patient.

In some embodiments, the matrix and methods can be used for bone inhibition. For example, the matrix is used as an inhibitor of osteoclast and/or fibroblast cell migration into a surgical site, thereby reducing or eliminating regrowth. In various embodiments, the matrix preserves the volumetric space that a spinal bone and/or soft tissue decompression procedure creates to relieve pain. In some embodiments, bone inhibition is at about 1%, 5%, 10%, 15%, 20%, 25%, 30%, 35%, 40%, 45%, 50%, 55%, 60%, 65%, 70%, 75%, 80%, 85%, 90%, 95% and/or 100%.

In various embodiments, a method of treating adhesions in a patient in need thereof is provided. The method comprising: administering to the patient a foldable or flexible biodegradable polymer matrix comprising a first layer comprising collagen and a second layer comprising collagen and dextran, wherein the dextran is loaded in the second layer in an amount of from about 5% to about 90% by weight based on a total weight of the matrix, wherein the matrix is configured to release and/or retain from about 20% to about 90% of the dextran loaded in the matrix within 24 to 48 hours.

In some embodiments, the dextran comprises dextran sulfate comprising from about 5.0 wt. % to about 70 wt. % of the total solid in the biodegradable polymer; the content of dextran sulfate is from about 0.5% to about 2.0% by weight; and/or the dextran sulfate has a molecular weight greater than about 500,000 Daltons.

In various embodiments, the matrix comprises purified type I bovine fibrillar collagen comprising from about 0.5% to about 2.0% by weight of the matrix, and releases free dextran and retains bound dextran. In some embodiments, the ratio of free dextran to bound dextran is at least from about 90:10, or from about 80:20, or from about 70:30, or from about 60:40.

Adhesions

Adhesions are abnormal, fibrous bands of scar tissue that can form inside the body as a result of the healing process that often follows open or minimally invasive surgical procedure including abdominal, gynecologic, cardiothoracic, spinal, plastic, vascular, ENT, ophthalmologic, urologic, neuro, or orthopedic surgery. Adhesions are typically connective tissue structures that form between adjacent injured areas within the body. Briefly, localized areas of injury trigger an inflammatory and healing response that culminates in healing and scar tissue formation. If scarring results in the formation of fibrous tissue bands or adherence of adjacent anatomical structures (that should normally be separate), adhesion formation is said to have occurred.

Adhesions can range from flimsy, easily separable structures to dense, tenacious fibrous structures that can only be separated by surgical dissection. Adhesion-related complications may include, for example, small bowel obstruction, infertility, chronic pelvic pain or back pain, and other complications. Adhesions from a previous procedure can also complicate a second surgery, whether the surgery is planned or unexpected. In addition, the abnormal orientation of tissues and organs caused by adhesions may lead to further discomfort and chronic pain.

"Reducing adhesions" refers to administering a composition so as to cause a reduction in the number of adhesions, extent of adhesions (e.g., area), and/or severity of adhesions (e.g., thickness or resistance to mechanical or chemical disruption) relative to the number, extent, and/or severity of adhesions that would occur without such administration. In various embodiments, reducing adhesions may be part of a protocol and also include performing a procedure (e.g., subsequent surgery to reduce adhesions). The composition or procedure may inhibit formation, or growth of adhesions following an adhesion promoting stimulus, may inhibit progression of adhesions, and/or may inhibit recurrence of adhesions following their spontaneous regression or following mechanical or chemical disruption.

"Preventing adhesions" refers to administering a therapeutic composition prior to formation of adhesions in order to reduce the likelihood that adhesions will form in response to a particular insult, stimulus, or condition. In various embodiments, preventing adhesions may be part of a protocol and also include performing a procedure (e.g., surgery to reduce adhesions). It will be appreciated that "preventing adhesions" does not require that the likelihood of adhesion formation is reduced to zero. Instead, "preventing adhesions" refers to a clinically significant reduction in the likelihood of adhesion formation following a particular insult or stimulus, e.g., a clinically significant reduction in the incidence or number of adhesions in response to a particular adhesion promoting insult, condition, or stimulus.

In various embodiments, the matrix can act as an adhesion barrier that can be administered or applied to the target tissue site before, during or after the surgery to reduce, prevent or treat adhesions. In some embodiments, the matrix, in addition to the dextran, creates a barrier that works by separating opposing tissue surfaces or tissue-organ surfaces while injured tissues heal. Ingrowth of scar tissue and the formation or reformation of adhesions immediately adjacent to the matrix is thus prevented.

In various embodiments, the adhesion matrix comprises a thin film or sponge composed of chemically modified sugars, in addition to the dextran, some of which occur naturally in the human body. The film or sponge adheres to tissues to which it is applied, and is slowly absorbed into the body over a period of about a week.

Another type of matrix is made of an amorphous bioresorbable copolymer, 70:30 poly(L-lactide-co-D,L-lactide), which is designed to match the natural lactic acid produced in the body. As an inert material, the body accepts the polymer and processes it through the normal channels of bulk hydrolysis, followed by further breakdown in the liver into $CO_2$ and $H_2O$. Still another type of matrix is based on PEG, which may be applied as two liquids, which are simultaneously sprayed onto the target area to form a soft adherent hydrogel. Within about one week, the hydrogel undergoes hydrolysis and is cleared from the body by the kidneys.

Sterilization

The matrix and/or medical device to administer the drug may be sterilizable. In various embodiments, one or more components of the matrix, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the matrix includes a gelatin capsule.

Other methods may also be used to sterilize the matrix and/or one or more components of the device, including, but not limited to, gas sterilization, such as, for example, with ethylene oxide or steam sterilization.

In various embodiments, a kit is provided that may include additional parts along with the matrix and/or medical device combined together to be used to implant the matrix. The kit may include a canister holding the matrix and any other instruments needed for the localized drug delivery in a first compartment. A second compartment may include gloves, drapes, wound dressings and other procedural supplies for maintaining sterility of the implanting process, as well as an instruction booklet. A third compartment may include additional cannulas and/or needles. A fourth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility. In some embodiments, a kit is provided with instruction to use an injectable drug from another kit.

The following examples are provided by way of illustration and are not intended to limit the present disclosure in any way unless specified.

EXAMPLES

Preparation of an Adhesion Barrier by Incorporating Dextran Sulfate into Type I Bovine Collagen Sponge Example 1

Dextran sulfate having molecular weight in excess of 500,000 was dissolved in 0.05M acetic acid to make a final concentration ranging from 0.05% to 2.0% by weight. Purified type I bovine fibrillar collagen was added into 0.05M acetic acid to make a final concentration ranging from 0.5% to 2.0% by weight as shown in Table I below. The collagen solution was dispersed at 20,000 rpm and 0° C.-10° C. for 2 hours using a homogenizer. The dextran sulfate solution was then added drop-wise into the collagen solution while the homogenizer was kept at 20,000 rpm and the temperature was kept at from about 0° C. to about 10° C. A white slurry was formed upon the completion of adding all the dextran sulfate solution into the collagen solution. The mixture was dispersed for another hour at 20,000 rpm and at temperatures from about 0° C. to about 10° C., and degased under vacuum at room temperature for an hour. The dextran sulfate and collagen slurry was poured into trays and lyophilized for 24 hours to form a collagen sponge comprising dextran sulfate. Crosslinking to form a membrane upon the dextran sulfate containing collagen sponge was then carried out by either dehydration heat treatment at 105° C. for 24 hours or by chemical crosslinking Chemical crosslinking could be achieved by reacting the collagen sponge comprising dextran sulfate with carbodiimide, glutaradehyde, or formalin. The dextran sulfate content ranged from 2.0% to 80.0% of the total solid in the adhesion barrier made using the above method.

TABLE I

| | | | DS Conc. | | | | | | |
|---|---|---|---|---|---|---|---|---|---|
| | | [mg/mL] | 0.5 | 2.5 | 5 | 10 | 15 | 20 | 25 |
| | | [w/v] | 0.05% | 0.25% | 0.5% | 1.0% | 1.5% | 2.0% | 2.5% |
| Collagen Conc. [w/v %] | 0.5% | % DS in Solid | 9% | 33% | 50% | 67% | 75% | 80% | 83% |
| | 1% | | 5% | 20% | 33% | 50% | 60% | 67% | 71% |

As illustrated in the above example, a sponge configuration allows for the adhesion prevention device to occupy a larger volumetric space than a thin sheet adjacent to the nerve structure being protected. The biodegradable porous sponge can also absorb body fluids at the surgical site and stay in place better on the nerve or vital structure. Some dextran sulfate will be released upon implantation but the adhesion barrier containing the collagen biodegradable porous matrix will slowly release dextran sulfate as the collagen resorbs over time. The length of time release is dependent on the degree of collagen crosslinking performed inside the collagen biodegradable matrix and also with respect to the membrane formed upon the collagen biodegradable matrix to provide the adhesion barrier describe in this disclosure. Cell migration into the sponge and surgical area will be minimized due to the presence of dextran sulfate on the sponge and its slow release over time. The lower dose of dextran sulfate will still allow desired adjacent tissue repair to occur.

Preparation of Adhesion Barriers Comprising Dextran Sulfate/Collagen Sponge Formulations Example 2

Three separate adhesion barriers were prepared in a similar matter as described in Example 1. The first formulation (Formulation #1) had a dextran sulfate (DS) content of 65% by weight and was crosslinked using DHT. The second formulation (Formulation #2) was crosslinked using carbodiimide and had a DS content of 30%. The third formation (Formulation #3) was crosslinked using carbodiimide and had a DS content of 10%.

As illustrated in FIG. 4, the three DS/collagen sponge formulations contained different burst release rates in vitro. The sponges were incubated in PBS at 37° C., and elution solutions were collected at different time points. DS contents in the elution solutions were quantified using 1,9-dimethylmethylene blue (DMMB) assay at OD525. A second sponge was digested using proteinase K, and the DS content in the sponge was quantified and used as total DS. The data were expressed as the percentage of DS released into the solution over the total DS in the sponge. The burst release rates at day 1 were 81% for Formulation #1, 39% for Formulation #2 and 29% for Formulation #3. Formulation #1 showed the best burst release rate for adhesion prevention. In various embodiments, Formulation #1 contained a free to bound dextran sulfate ratio of about 30:70, Formulation #2 contained a free to bound dextran sulfate ratio of about 50:50 and Formulation #3 comprised a free to bound dextran sulfate ratio of about 80:20.

Example 3

Figure 5:
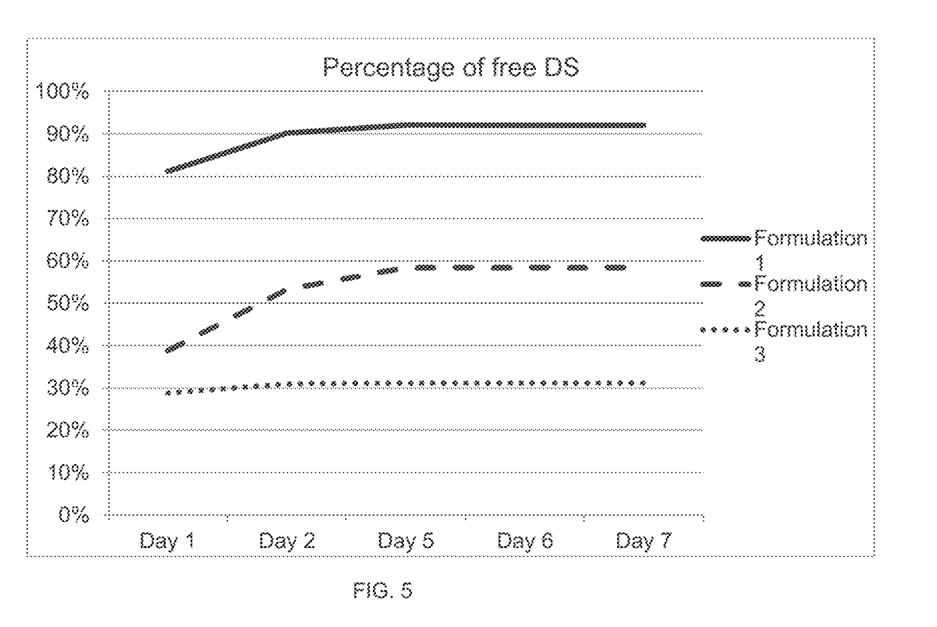
FIG. 5 depicts a graphical representation of the percentage of free dextran sulfate in three dextran sulfate collagen sponge formulations where each formulation comprises different burst release rates in vitro over a period of time.

As exemplified in FIG. 5, the percentage of immobilized/retained DS in a sponge Formulation #1-2 (the combination of Formulation #1 and Formulation #2) was examined. DS/collagen sponges were incubated in PBS at 37° C., and sponge samples were taken at different time points from 4 hrs to 14 days. Collagen was digested completely using proteinase K. DS content in the sponge was quantified using 1,9-dimethylmethylene blue (DMMB) assay at OD525. The data were expressed as the average percentage of DS retained in the sponge over the initial DS content±SD (N=3). The data showed that about 5% DS was retained with the sponge for up to 14 days after a burst release within 4 hrs, which reflected a high burst release profile.

Example 4

Figure 6:
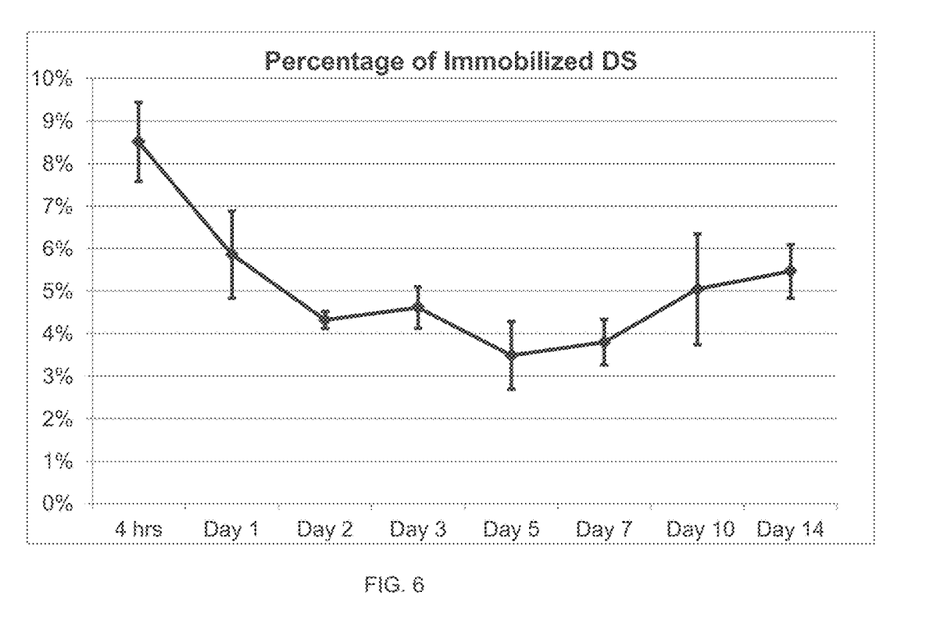
FIG. 6 provides a graphical representation of the percentage of immobilized/retained dextran sulfate in a sponge formulation over a period of time.

As illustrated in FIG. 6, the percentage of expected DS content in a DS/collagen sponge was examined. Uniformity of DS contents in DS/collagen sponges were fabricated using the method described above. Samples (8 mm in diameter) were taken from 10 different locations of a single DS/collagen sponge. Collagen was digested using proteinase K and DS contents were quantified using DMMB assay. DS content ranged from 101% to 133% of expected values with an average of 116%±3% (SD).

Example 5

Figure 7:
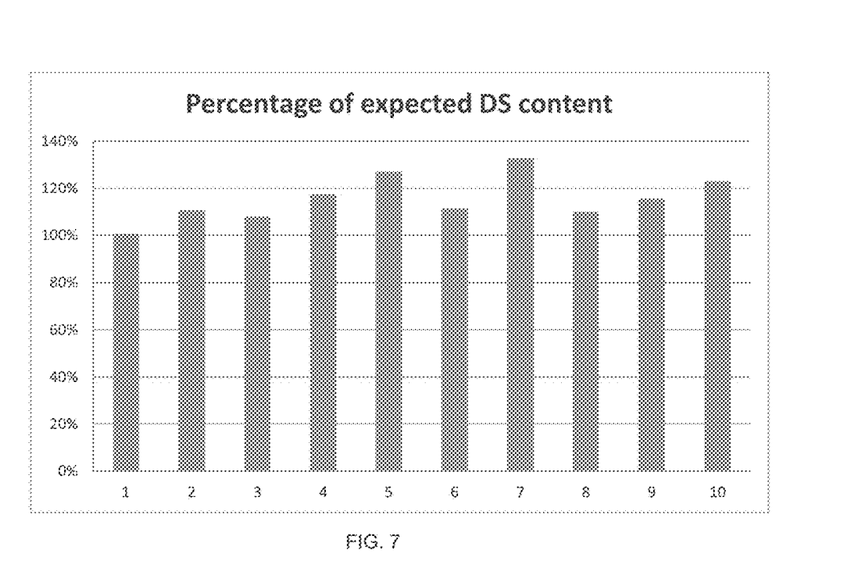
FIG. 7 provides a graphical representation of the uniformity of dextran sulfate contents in a dextran sulfate/collagen sponge and the percentage of expected dextran sulfate content within 10 different locations on the sponge.

As shown in FIG. 7, the efficacy of Formulations #1, #2 and #3 (prepared in the same manner as described in Example 2) in adhesion prevention in the rabbit laminectomy model was examined. A two-level laminectomy was performed at L4 and L6 in mature New Zealand White rabbits. In each animal, one level was treated with either Formulation #1, #2 or #3, and the other level was left untreated to server as an internal control. The treated and control levels were randomized from animal to animal. The study was terminated at 4 weeks post-surgery. The tenacity and the extent of adhesion were scored by three assessors blinded of treatments independently based on a 0-3 grading system. Tenacity score: 0=no adhesion; 1=minimal, easily detachable; 2=moderate, blunt dissection; 3=tenacious, sharp dissection. Extent score (% of the area covered with adhesion/scar tissue): 0=no adhesion; 1=<25%; 2=25-75%; 3=>75%. Formulation #1 (DS content of 65% and 35% collagen) showed the best efficacy in adhesion prevention, and no implanted materials were detected macroscopically at 4 weeks post implantation.

Example 6

Figure 8:
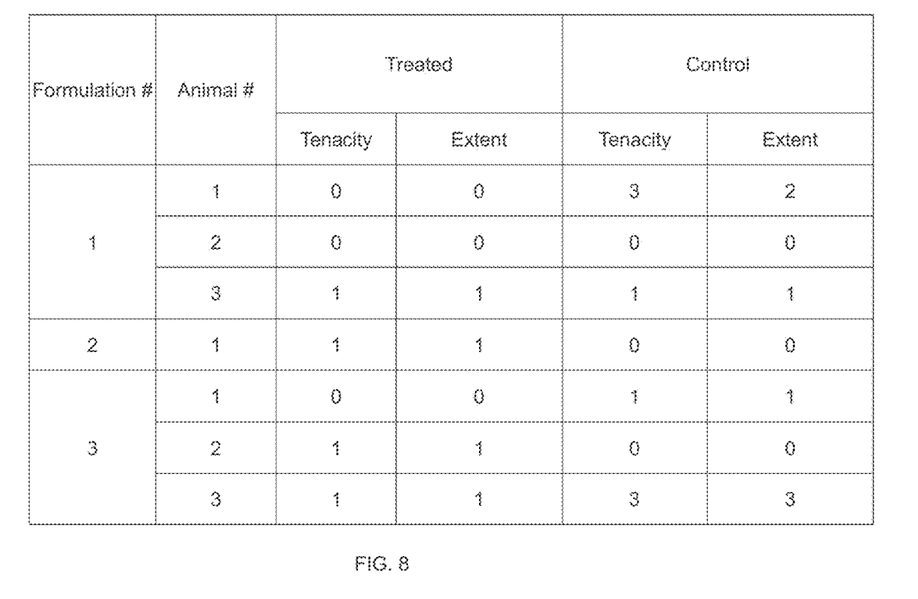
FIG. 8 provides a table that exemplifies the efficacy of 3 formulations in adhesion prevention in a rabbit laminectomy model.

As shown in FIG. 8, the efficacy of Formulation #1 with 3 different DS contents was examined. DS contents were 50%, 67% and 75% for Formulations #1-1, #1-2 and #1-3. Animals #1-3 were sacrificed at 4 weeks, and animals #4-6 were sacrificed at 8 weeks post-surgery. All 3 showed efficacy in adhesion prevention in the rabbit laminectomy model. Formulation #1-2 showed adhesion prevention for up to 8 weeks even though the implant was gone by 4 weeks.

Example 7

Figure 9:
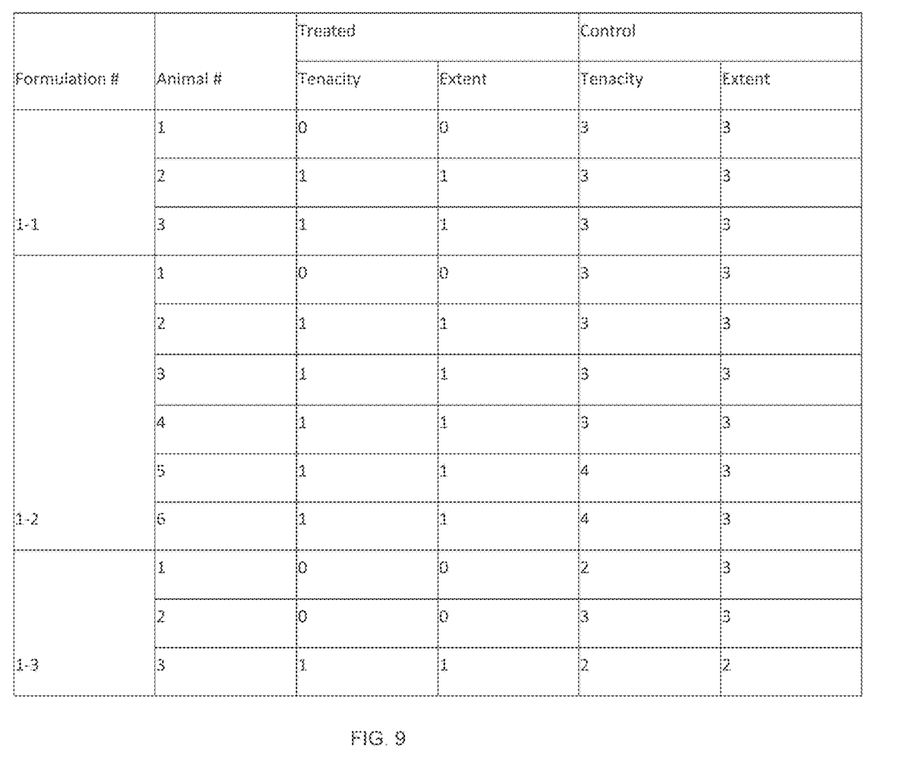
FIG. 9 provides a table that exemplifies the efficacy of a formulation with 3 different dextran sulfate contents.
Figure 10:
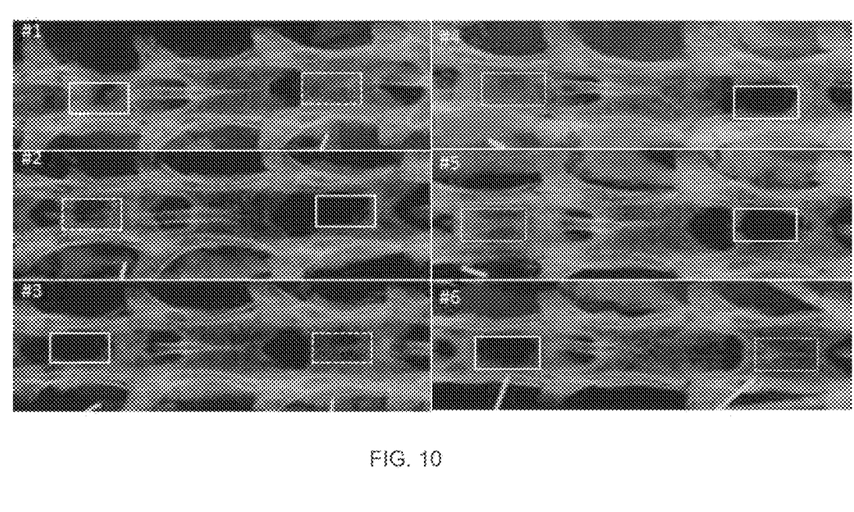
FIG. 10 is a representation of x-ray images showing inhibition of bone regrowth of laminectomy defects where solid boxes showed laminectomy defects treated with a formulation and dotted boxes showed those of controls.

FIG. 9 is a representative of x-ray images showing inhibition of bone regrowth of a laminectomy defect. The solid boxes show laminectomy defects treated with Formulation #1-2, and dotted boxes showed those of controls. Animals #1-3 were sacrificed at 4 weeks, and #4-6 were sacrificed at 8 weeks post-surgery. The results showed that Formulation #1-2 reduced and/or prevented bone regrowth in a laminectomy. All formulations inhibited bone growth. The formulation with about 67% dextran and about 33% collagen had no bone growth after 8 weeks. This was a surprising result and will be useful in preventing regrowth of bone in laminectomy, laminotomy, discectomy, facetectomy or other procedure where bone growth is not desired for a certain period of time.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A foldable or flexible biodegradable polymer matrix for reducing, preventing or treating adhesions in a patient in need thereof, the matrix comprising a first layer comprising collagen; a second layer comprising dense collagen; and a third layer comprising collagen and dextran, wherein the dextran is loaded in the third layer in an amount of from about 5% to about 90% by weight based on a total weight of the matrix, and the matrix is configured to be folded into a wrap configuration such that the third layer is on the outside of the wrap and the first layer is on the inside of the wrap and the second layer is disposed between the first layer and the third layer; and the matrix is configured to release from about 5% to about 90% of the dextran loaded in the matrix, wherein the first layer comprises pores that have a pore size from about 250 to about 1000 microns, wherein the matrix is folded into a wrap configuration and the third layer is less porous than the first layer but is more porous than the second layer.

2. A matrix of claim 1, wherein the matrix (i) is a multi-layered sheet; (ii) is a multi-layered sponge; (iii) is in tubular form; (iv) is in strip or sheet form; (v); the matrix reduces cell growth into the matrix by retaining dextran; or (vi) the matrix is configured to release from about 20% to about 90% of the dextran loaded in the matrix within 24 to 48 hours.

3. A matrix of claim 1, wherein the dextran comprises dextran sulfate comprising from about 5.0 wt. % to about 70 wt. % of the matrix and the content of dextran sulfate is from about 0.5% to about 2.0% by weight.

4. A matrix of claim 1, wherein the first layer is porous to facilitate cell infiltration and attachment to the first layer and the first layer comprises pores having a pore size from about 250 to about 500 microns.

5. A matrix of claim 1, wherein the second layer is non-porous and prevents diffusion of the dextran into the first layer.

6. A matrix of claim 1, wherein the third layer comprises pores that have a pore size from about 0.05 to about 200 microns.

7. A matrix of claim 1, wherein the second layer and the third layer comprise pores that have a pore size from about 0.05 to about 200 microns, the first layer being more porous than the third layer, the dextran being loaded in the second layer and the third layer in an amount of from about 5% to about 90% by weight based on a total weight of the matrix and the dextran configured to release from about 5% to about 90% within 24 to 48 hours and the matrix reduces cell growth therein, wherein the third layer is the outer most layer.

* * * * *

UNITED STATES PATENT AND TRADEMARK OFFICE
CERTIFICATE OF CORRECTION

PATENT NO. : 10,034,968 B2  
APPLICATION NO. : 15/427809  
DATED : July 31, 2018  
INVENTOR(S) : Vickers Page 1 of 1

It is certified that error appears in the above-identified patent and that said Letters Patent is hereby corrected as shown below:

In the Specification

In Column 1, Line 5, delete "DEVICE."" and insert -- DEVICE", now Pat. No. 9,566,296. --, therefor.

In Column 7, Line 48, delete "(FIN)" and insert -- (HN) --, therefor.

In Column 7, Line 56, delete "FIN" and insert -- HN --, therefor.

In Column 9, Line 37, delete "9.0 9.25," and insert -- 9.0, 9.25, --, therefor.

In Column 11, Line 3, delete "collage, native collagen or modified collage" and insert -- collagen, native collagen or modified collagen --, therefor.

In Column 11, Line 61, delete "(PG)," and insert -- (PGA), --, therefor.

In Column 12, Line 40, delete "and or" and insert -- and/or --, therefor.

In Column 13, Lines 38-39, delete "collage, native collagen or modified collage" and insert -- collagen, native collagen or modified collagen --, therefor.

In Column 22, Line 45, delete "crosslinking Chemical" and insert -- crosslinking. Chemical --, therefor.

In the Claims

In Column 25, Line 18, in Claim 2, delete "(v);" and insert -- (v) --, therefor.

Signed and Sealed this  
Twenty-ninth Day of January, 2019

Andrei Iancu  
*Director of the United States Patent and Trademark Office*